(12) United States Patent
Schülein et al.

(10) Patent No.: US 6,296,671 B1
(45) Date of Patent: Oct. 2, 2001

(54) ENZYMATIC TREATMENT METHOD

(75) Inventors: Martin Schülein, Copenhagen; Henrik Kristensen, Charlottenlund, both of (DK)

(73) Assignee: Novorymeo A/S, Bagsvaerd (DK)

( * ) Notice: Subject to any disclaimer, the term of this patent is extended or adjusted under 35 U.S.C. 154(b) by 0 days.

(21) Appl. No.: 09/542,767

(22) Filed: Apr. 4, 2000

Related U.S. Application Data

(63) Continuation of application No. PCT/DK00/00136, filed on Mar. 22, 2000
(60) Provisional application No. 60/125,884, filed on Mar. 24, 1999.

(30) Foreign Application Priority Data

Mar. 22, 1999 (DK) ................................. PA 00390

(51) Int. Cl.$^7$ ........................................ D06L 1/12
(52) U.S. Cl. ........................... 8/139; 510/392; 435/263; 134/22.14; 8/181
(58) Field of Search ............................ 510/392; 435/270; 8/139, 181; 134/22-14

(56) References Cited

U.S. PATENT DOCUMENTS 3,867,553   2/1975   Hitze et al. .......................... 426/44

FOREIGN PATENT DOCUMENTS

| 4012 351 A1 | 10/1991 | (DE) . |
| 0 421 919 A2 | 4/1991 | (EP) . |
| 10313858-A | * 5/1997 | (JP) . |
| WO 95/16808 | 6/1995 | (WO) . |
| WO 98/06809 | 2/1998 | (WO) . |

OTHER PUBLICATIONS

Abstract of Japanese Patent JP 10313858 A, 1997.

* cited by examiner

*Primary Examiner*—Yogendra N. Gupta
*Assistant Examiner*—Eisa Elhilo
(74) *Attorney, Agent, or Firm*—Elias J. Lambiris; Jason I. Gargell

(57) ABSTRACT

Polymethylgalacturonases belonging to family 28 of polysaccharide lyases and comprising the amino acid sequence of SEQ ID NO:1 or an amino acid sequence having at least 70% sequence identity with SEQ ID NO:1 show good performance in industrial processes such as laundering and textile processing.

8 Claims, No Drawings

SEQUENCE LISTING

<160> NUMBER OF SEQ ID NOS: 1

<210> SEQ ID NO 1
<211> LENGTH: 360
<212> TYPE: PRT
<213> ORGANISM: Trichisporon penicillatum

<400> SEQUENCE: 1

```
Met His Leu Ser Asn Ile Val Ser Ala Ala Ser Leu Ala Ala Leu Ala
1               5                   10                  15

Ala Ala Ala Pro Ala Glu Leu Glu Arg Arg Gln Val Asn Cys Val Phe
            20                  25                  30

Thr Asn Tyr Glu Gln Ile Ala Ser His Thr Ala Asn Cys Asp Thr Ile
        35                  40                  45

Thr Leu Asn Asn Ile Asn Val Pro Ala Gly Lys Glu Leu Asp Leu Thr
    50                  55                  60

Asn Leu Lys Pro Gly Ala Asn Val Val Phe Glu Gly Arg Thr Thr Phe
65                  70                  75                  80

Gly Tyr Ala Glu Trp Ala Gly Pro Leu Ile Met Val Ser Gly Asp Asp
                85                  90                  95

Ile Thr Val Ser Gln Thr Pro Gly Ser Val Ile Asp Gly Glu Gly Ala
            100                 105                 110

Arg Trp Trp Asp Asn Lys Gly Ala Asn Gly Gly Lys Val Lys Pro Arg
        115                 120                 125

Leu Phe Tyr Ala His Asn Leu Asp Asn Ser His Ile Asn Gly Leu His
    130                 135                 140
```

-continued

```
Ile Lys Asn Thr Pro Val Phe Gly Phe Ser Ile Asp Ser Lys Asn Leu
145                 150                 155                 160

Ile Ile Asp Gly Val Arg Ile Asp Asn Ser Asp Gly Asp Thr Gln Gly
                165                 170                 175

Ala Phe Asn Thr Asp Ala Phe Asp Val Ser Gln Ser Tyr Asn Val Thr
                180                 185                 190

Ile Gln Asn Ala Trp Val His Asn Gln Asp Asp Cys Leu Ala Ile Asn
        195                 200                 205

Gln Gly Glu Leu Ile His Phe Leu Asn Gly Tyr Cys Tyr Gly Gly His
        210                 215                 220

Gly Leu Ser Ile Gly Ser Val Gly Gly Gly Asn Val Val Ser Asp Val
225                 230                 235                 240

Val Ile Ala Asp Ser Gln Ile Ile Asn Ser Gln Asn Gly Val Arg Ile
                245                 250                 255

Lys Thr Lys Ser Gly Gln Thr Gly Glu Val Arg Gly Ile Thr Tyr Arg
                260                 265                 270

Asn Ile Phe Leu Ser Gly Ile Thr Asp Tyr Gly Leu Ile Val Gln Gln
        275                 280                 285

Asp Tyr Asn Asn Pro Gly His Ala Thr Asn Ser Ile Lys Ile His Asp
        290                 295                 300

Ile Thr Phe Asp Asn Val His Gly Thr Ala Thr Gln His Gly Phe Asn
305                 310                 315                 320

Ile Ala Ile Phe Cys Gly Asp Gly Ser Cys Tyr Asp Trp Thr Trp Asn
                325                 330                 335

Glu Val Lys Ile His Gly Ala Arg Asp Tyr Lys Cys Gln Asn Val Pro
                340                 345                 350

Ser Ser Ala Ser Cys Gln Ala Ser
        355                 360
```

ENZYMATIC TREATMENT METHOD

CROSS-REFERENCE TO RELATED APPLICATIONS

This application is a continuation of PCT/DK00/00136 filed on Mar. 22, 2000 and claims priority under 35 U.S.C. 119 of Danish application no. PA 1999 00390 filed on Mar. 22, 1999, and U.S. application Ser. No. 60/125,884 filed on Mar. 24, 1999, the contents of which are fully incorporated herein by reference.

The present invention relates to a process for using polymethylgalacturonases in the textile, detergent and cellulose fiber processing industries and to a cleaning composition comprising a polymethylgalacturonase.

BACKGROUND OF THE INVENTION

Pectin polymers are important constituents of plant cell walls. Pectin is a hetero-polysaccharide with a backbone composed of alternating homogalacturonan (smooth regions) and rhamnogalacturonan (hairy regions). The smooth regions are linear polymers of 1,4-linked alpha-D-galacturonic acid. The galacturonic acid residues can be methyl-esterified on the carboxyl group to a varying degree, usually in a non-random fashion with blocks of polygalacturonic acid being completely methyl-esterified.

Pectinases can be classified according to their preferential substrate, highly methyl-esterified pectin or low methyl-esterified pectin and polygalacturonic acid (pectate), and their reaction mechanism, beta-elimination or hydrolysis. Pectinases can be mainly endo-acting, cutting the polymer at random sites within the chain to give a mixture of oligomers, or they may be exo-acting, attacking from one end of the polymer and producing monomers or dimers. Several pectinase activities acting on the smooth regions of pectin are included in the classification of enzymes provided by the Enzyme Nomenclature (1992) such as polymethylgalacturonase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and exo-poly-alpha-galacturonosidase (EC 3.2.1.82).

Glycosyl hydrolases are classified into families according to their three-dimensional structure or folding; conventionally the Clustal W method is used the for family determination. Based on amino acid sequence alignment and the Clustal W method, a polypeptide or protein can be classified into a specific glycosyl hydrolase family, ie either a known family or a novel and hitherto unknown family (The Sanger Centre: Protein Families Database of alignments and HMMs; www.sanger.ac.uk). At present known polymethylgalacturonases belong to family 28 of glycosyl hydrolases (ExPASy—molecular biology WWW server of the Swiss Institute of Bioinformatics (SIB)).

Polymethylgalacturonases have been cloned from various microbial organisms. However, up till very recently all polymethylgalacturonases were known as requiring divalent cations for maximum activity, calcium ions being the most stimulatory. In contrast hereto, Japanese patent application Kokai 10-313858 discloses a novel polymethylgalacturonase of family 28 which is believed not to require the presence of divalent cations for maximum activity, ie this novel enzyme is capable of exerting its action in an aqueous solution which further comprises calcium chelators. Calcium chelators are known to be present in a number of industrial processes including scouring of cotton.

It is an object of the present invention to provide improved industrial enzymatic processes which are more efficient and/or have higher cost-benefit than the hitherto known processes.

SUMMARY OF THE INVENTION

The inventors have now found that pectin hydrolases such as polymethylgalacturonases exhibiting hydrolytic activity against protopectic acid and methylated polygalacturonic acid show excellent performance in various industrial processes, and are especially useful for the treatment of cellulosic material, especially cellulose-containing fiber, yarn, woven or non-woven fabric, treatment of mechanical paper-making pulps or recycled waste paper, and for retting of fibres. The enzymatic treatment can be carried out during the processing of cellulosic material into a material ready for garment manufacture or fabric manufacture, e.g. in the desizing or scouring step; or during industrial or household laundering of such fabric or garment.

It is contemplated that the polymethylgalacturonase enzymes described herein are very effective for use in an enzymatic scouring process in the preparation of cellulosic material e.g. for proper response in subsequent dyeing operations. Further, it is contemplated that detergent compositions comprising the polymethylgalacturonases described herein are capable of removing or bleaching certain soils or stains present on laundry, especially soils and spots resulting from pectin or highly methylated polygalacturonic acid containing food, plants, and the like. It is also contemplated that treatment with detergent compositions comprising the polymethylgalacturonase enzyme can prevent binding of certain soils to the cellulosic material. The polymethylgalacturonase enzymes are also useful as ingredients in hard surface cleaning compositions having the effect of removing or assisting in removing certain soils or stains from hard surfaces in need of cleaning.

Accordingly, the present invention relates to a process for degradation or modification of fibres, yarn or woven or non-woven fabric comprising plant material, the process comprising the step of subjecting the fibres or fabric to a treatment, in an aqueous solution, with an effective amount of a polymethylgalacturonase enzyme comprising the amino acid sequence of SEQ ID NO:1 or an amino acid sequence having at least 70% sequence identity with SEQ ID NO:1.

In a further aspect, the present invention relates to a cleaning or laundering detergent composition comprising an enzyme having substantial polymethylgalacturonase activity and a surfactant.

DEFINITIONS

The term "enzyme core" denotes the part of a single- or multi-domain structure polypeptide exhibiting enzymatic activity which part is a single domain part containing the catalytically active domain. Accordingly, the enzyme core does not contain other domains than the catalytic domain.

The term "pectin" denotes pectate, polygalacturonic acid, and pectin which may be esterified or methylated to a higher or lower degree.

The term "pectinase" denotes a pectinase enzyme defined according to the art where pectinases are a group of enzymes that cleave glycosidic linkages of pectic substances mainly poly(1,4-alpha-D-galacturonide and its derivatives(Sakai et al., Pectin, pectinase and protopectinase: production, properties and applications, pp 213–294 in: Advances in Applied Microbiology vol: 39,1993).

For purposes of the present invention, the degree of identity (percent sequence identity) between two amino acid sequences is determined by conventional methods, by means of computer programs known in the art such as GAP provided in the GCG program package (Program Manual for the Wisconsin Package, Version 9.1, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 30 and GAP extension penalty of 1.

DETAILED DESCRIPTION OF THE INVENTION THE ENZYME

In the method of the present invention it is preferred to use a polymethylgalacturonase having hydrolytic activity against protopectic acid and methylated polygalacturonic acid. Such a polymethylgalacturonase may be classified according to the Enzyme Nomenclature as EC 3.2.1.15 which is defined as catalysing the reaction random hydrolysis of 1,4-alpha-D-galactosiduronic linkages in pectate and other galacturonans; or as EC 4.2.2.2 which is defined as catalysing the reaction eliminative cleavage of pectate to give oligosaccharides with 4-deoxy-alpha-D-gluc-4-enuronosyl groups at their non-reducing ends. It is known that the polymethylgalacturonases belonging to EC 3.2.1.15 or EC 4.2.2.2 are normally only capable of degrading demethylated pectins including demethylated polygalacturonic acid.

However, certain polymethylgalacturonases, especially certain polymethylgalacturonases belonging to family 28 of glycosyl hydrolases, are capable of degrading methylated pectins such as pectins having a degree of esterification of at least 50% or even of at least 75%. Such useful polymethylgalacturonases may further possess the very valuable property of being able to exert its enzymatic activity in the presence of a chelating agent, especially a calcium chelator.

A specific example of such a useful polymethylgalacturonase is the enzyme represented by the amino acid sequence of the attached SEQ ID NO:1. It is contemplated that polymethyl galacturonases which have a degree of identity to the mature part of the polypeptide represented by the amino acid sequence of SEQ ID NO:1 of at least 70%, preferably at least 80%, are also useful, i.e. they exhibit hydrolytic activity against protopectic acid and methylated polygalacturonic acid. In a preferred embodiment, the useful polymethylgalacturonases have an amino acid sequence which differs at the most by five amino acids, preferably by four amino acids, more preferably by three amino acids, even more preferably by two amino acids, and most preferably by one amino acid from the amino acid sequence of SEQ ID NO:1 representing the mature enzyme.

The polymethylgalacturonase of SEQ ID NO:1 is encoded by a gene derived from a strain of the filamentous fungus *Trichosporon penicillatum*, also named *Geotrichum penicillatum*, especially the publicly available strain deposited as ATCC 42397. The genomic DNA sequence of this gene (1083 base pairs) is disclosed in published Japanese patent application Kokai 10-313858 the disclosure of which is hereby incorporated by reference in its entirety. This polymethylgalacturonase is stable between pH 4 and pH 7, measured at 5° C., 30 minutes, and exhibits optimum activity at pH 5, measured at 37° C., and optimum activity at a temperature of 5° C., measured at pH 5, 60 minutes.

HOW TO USE A SEQUENCE TO GET OTHER RELATED SEQUENCES

The disclosed sequence information in published Japanese patent application Kokai 10-313858 relating to a polynucleotide sequence encoding a polymethylgalacturonase can be used as a tool to identify other homologous polymethylgalacturonase enzymes. For instance, polymerase chain reaction (PCR) can be used to amplify sequences encoding other homologous polymethylgalacturonase enzymes from a variety of microbial sources.

ENZYME PREPARATION

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant polymethylgalacturonase, but which microorganism simultaneously produces other enzymes, e.g. pectin lyases, pectate lyases, proteases, or cellulases, being naturally occurring fermentation products of the microorganism, i.e. the enzyme complex conventionally produced by the corresponding naturally occurring microorganism.

In the process of the present invention, it may be advantageous to use an enzyme preparation which, in addition to the content of polymethylgalacturonase, further comprises one or more enzymes selected from the group consisting of proteases, cellulases (endo-β-1,4-glucanases), β-glucanases (endo-β-1,3(4)-glucanases), lipases, cutinases, peroxidases, laccases, amylases, glucoamylases, other pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectate lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are mono-component enzyme(s) which is/are mixed with the other enzyme(s) to form an enzyme preparation with the desired enzyme blend.

Use in the Detergent or Cleaning Industry

In further aspects, the present invention relates to a cleaning, laundering or detergent composition comprising the polymethylgalacturonase enzyme or enzyme preparation of the invention, to a process for machine treatment of fabrics comprising treating fabric during a washing cycle of a machine washing process with a washing solution comprising the polymethylgalacturonase described herein, and to cleaning compositions, including laundry, hard surface cleaner, personal cleansing and oral/dental compositions, comprising a polymethylgalacturonase described herein providing superior cleaning performance, i.e. superior stain removal.

Without being bound to this theory, it is believed that the disclosed polymethylgalacturonase is capable of effectively degrading or hydrolysing almost any soiling or spots containing highly methylated pectins and, accordingly, of cleaning laundry comprising such soilings or spots.

The cleaning compositions of the invention must contain at least one additional detergent component. The precise nature of these additional components, and levels of incorporation thereof will depend on the physical form of the composition, and the nature of the cleaning operation for which it is to be used.

The cleaning compositions of the present invention preferably further comprise a detergent ingredient selected from a selected surfactant, another enzyme, a builder and/or a bleach system.

The cleaning compositions according to the invention can be liquid, paste, gels, bars, tablets, spray, foam, powder or granular. Granular compositions can also be in "compact" form and the liquid compositions can also be in a "concentrated" form.

The compositions of the invention may for example, be formulated as hand and machine dishwashing compositions, hand and machine laundry detergent compositions including laundry additive compositions and compositions suitable for use in the soaking and/or pretreatment of stained fabrics, rinse added fabric softener compositions, and compositions for use in general household hard surface cleaning operations. Compositions containing such carbohydrases can also be formulated as sanitization products, contact lens cleansers and health and beauty care products such as oral/dental care and personal cleaning compositions.

When formulated as compositions for use in manual dishwashing methods the compositions of the invention preferably contain a surfactant and preferably other detergent compounds selected from organic polymeric compounds, suds enhancing agents, group II metal ions, solvents, hydrotropes and additional enzymes.

When formulated as compositions suitable for use in a laundry machine washing method, the compositions of the invention preferably contain both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components. Such compositions containing carbohydrase can provide fabric cleaning, stain removal, whiteness maintenance, softening, colour appearance, dye transfer inhibition and sanitization when formulated as laundry detergent compositions.

The compositions of the invention can also be used as detergent additive products in solid or lic id form. Such additive products are intended to supplement or boost the performance of conventional detergent compositions and can be added at any stage of the cleaning process.

If needed the density of the laundry detergent compositions herein ranges from 400 to 1200 g/litre, preferably 500 to 950 g/litre of composition measured at 20° C.

The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition. In the compact compositions, the filler salt is present in amounts not exceeding 15% of the total composition, preferably not exceeding 10%, most preferably not exceeding 5% by weight of the composition. The inorganic filler salts, such as meant in the present compositions are selected from the alkali and alkaline-earth-metal salts of sulphates and chlorides. A preferred filler salt is sodium sulphate.

Liquid detergent compositions according to the present invention can also be in a "concentrated form", in such case, the liquid detergent compositions according the present invention will contain a lower amount of water, compared to conventional liquid detergents. Typically the water content of the concentrated liquid detergent is preferably less than 40%, more preferably less than 30%, most preferably less than 20% by weight of the detergent composition.

Suitable specific detergent compounds for use herein are selected from the group consisting of the specific compounds as described in WO 97/01629 which is hereby incorporated by reference in its entirety.

Mannanase may be incorporated into the cleaning compositions in accordance with the invention preferably at a level of from 0.0001% to 2%, more preferably from 0.0005% to 0.5%, most preferred from 0.001% to 0.1% pure enzyme by weight of the composition.

The cellulases usable in the present invention include both bacterial and fungal cellulases. Preferably, they will have a pH optimum of between 5 and 12 and a specific activity above 50 CEVU/mg (Cellulose Viscosity Unit). Suitable cellulases are disclosed in U.S. Pat. No. 4,435,307, J610783384 and WO96/02653 which discloses fungal cellulase produced from Humicola insolens, Trichoderma, Thielavia and Sporotrichum, respectively. EP 739 982 describes cellulases isolated from novel Bacillus species. Suitable cellulases are also disclosed in GB-A-2075028; GB-A-2095275; DE-OS-22 47 832 and WO95/26398.

Examples of such cellulases are cellulases produced by a strain of Humicola insolens (Humicola grisea var. thermoidea), particularly the strain Humicola insolens, DSM 1800. Other suitable cellulases are cellulases originated from Humicola insolens having a molecular weight of about 50 kD, an isoelectric point of 5.5 and containing 415 amino acids; and a _43 kD endo-beta-1,4-glucanase derived from Humicola insolens, DSM 1800; a preferred cellulase has the amino acid sequence disclosed in PCT Patent Application No. WO 91/17243. Also suitable cellulases are the EGIII cellulases from Trichoderma longibrachiatum described in WO94/21801. Especially suitable cellulases are the cellulases having color care benefits. Examples of such cellulases are the cellulases described in WO96/29397, EP-A-0495257, WO91/17243, WO91/17244 and WO91/21801. Other suitable cellulases for fabric care and/or cleaning properties are described in WO96/34092, WO096/17994 and WO95/24471.

Said cellulases are normally incorporated in the detergent composition at levels from 0.0001% to 2% of pure enzyme by weight of the detergent composition.

Preferred cellulases for the purpose of the present invention are alkaline cellulases, i.e. enzyme having at least 25%, more preferably at least 40% of their maximum activity at a pH ranging from 7 to 12. More preferred cellulases are enzymes having their maximum activity at a pH ranging from 7 to 12. A preferred alkaline cellulase is the cellulase sold under the tradename Carezyme® by Novo Nordisk A/S.

Amylases ($\alpha$ and/or $\beta$) can be included for removal of carbohydrate-based stains. WO94/02597, Novo Nordisk A/S published Feb. 3, 1994, describes cleaning compositions which incorporate mutant amylases. See also WO95/10603, Novo Nordisk A/S, published Apr. 20, 1995. Other amylases known for use in cleaning compositions include both $\alpha$- and $\beta$-amylases. $\alpha$-Amylases are known in the art and include those disclosed in U.S. Pat. No. 5,003,257; EP 252,666; WO /91/00353; FR 2,676,456; EP 285,123; EP 525,610; EP 368,341; and British Patent specification no. 1,296,839 (Novo). Other suitable amylases are stability-enhanced amylases described in WO094/18314, published Aug. 18, 1994 and WO96/05295, Genencor, published Feb. 22, 1996 and amylase variants having additional modification in the immediate parent available from Novo Nordisk A/S, disclosed in WO95/10603, published April 1995. Also suitable are amylases described in EP 277 216, WO95/26397 and WO96/23873 (all by Novo Nordisk).

Examples of commercial α-amylases products are Purafect Ox Am® from Genencor and Termamyl®, Ban®, Fungamyl® and Duramyl®, all available from Novo Nordisk A/S Denmark. WO95/26397 describes other suitable amylases: α-amylases characterised by having a specific activity at least 25% higher than the specific activity of Termamyl® at a temperature range of 25° C. to 55° C. and at a pH value in the range of 8 to 10, measured by the Phadebas® α-amylase activity assay. Suitable are variants of the above enzymes, described in WO096/23873 (Novo Nordisk). Other amylolytic enzymes with improved properties with respect to the activity level and the combination of thermostability and a higher activity level are described in WO95/35382.

Preferred amylases for the purpose of the present invention are the amylases sold under the tradename Termamyl, Duramyl and Maxamyl and or the α-amylase variant demonstrating increased thermostability disclosed as SEQ ID No. 2 in WO96/23873.

Preferred amylases for specific applications are alkaline amylases, ie enzymes having an enzymatic activity of at least 10%, preferably at least 25%, more preferably at least 40% of their maximum activity at a pH ranging from 7 to 12. More preferred amylases are enzymes having their maximum activity at a pH ranging from 7 to 12.

The amylolytic enzymes are incorporated in the detergent compositions of the present invention a level of from 0.0001% to 2%, preferably from 0.00018% to 0.06%, more preferably from 0.00024% to 0.048% pure enzyme by weight of the composition.

The term xyloglucanase encompasses the family of enzymes described by Vincken and Voragen at Wageningen University [Vincken et al (1994) Plant Physiol., 104, 99–107] and are able to degrade xyloglucans as described in Hayashi et al (1989) Plant. Physiol. Plant Mol. Biol., 40, 139–168. Vincken et al demonstrated the removal of xyloglucan coating from cellulase of the isolated apple cell wall by a xyloglucanase purified from Trichoderma viride (endo-IV-glucanase). This enzyme enhances the enzymatic degradation of cell wall-embedded cellulose and work in synergy with pectic enzymes. Rapidase LIQ+ from Gist-Brocades contains an xyloglucanase activity.

This xyloglucanase is incorporated into the cleaning compositions in accordance with the invention preferably at a level of from 0.0001% to 2%, more preferably from 0.0005% to 0.5%, most preferred from 0.001% to 0.1% pure enzyme by weight of the composition.

Preferred xyloglucanases for specific applications are alkaline xyloglucanases, ie enzymes having an enzymatic activity of at least 10%, preferably at least 25%, more preferably at least 40% of their maximum activity at a pH ranging from 7 to 12. More preferred xyloglucanases are enzymes having their maximum activity at a pH ranging from 7 to 12.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is common practice to modify wild-type enzymes via protein or genetic engineering techniques in order to optimise their performance efficiency in the cleaning compositions of the invention. For example, the variants may be designed such that the compatibility of the enzyme to commonly encountered ingredients of such compositions is increased. Alternatively, the variant may be designed such that the optimal pH, bleach or chelant stability, catalytic activity and the like, of the enzyme variant is tailored to suit the particular cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing metal binding sites to increase chelant stability.

Use in the Textile and Cellulosic Fiber Processing Industries

The polymethylgalacturonase disclosed herein can be used in combination with other carbohydrate degrading enzymes (for instance arabinanase, xyloglucanase, pectinase) for biopreparation of fibers or for cleaning of fibers in combination with detergents. Cotton fibers consist of a primary cell wall layer containing pectin and a secondary layer containing mainly cellulose. Under cotton preparation or cotton refining part of the primary cell wall will be removed. The present invention relates to either help during cotton refining by removal of the primary cell wall or during cleaning of the cotton to remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

It is also contemplated that the enzyme described herein is useful in the cellulosic fiber processing industry for the pretreatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are a. Desizing (for woven goods) using polymeric size like e.g. starch, CMC or PVA is added before weaving in order to increase the warp speed; This material must be removed before further processing.

b. Scouring, the aim of which is to remove non-cellulosic aterial from the cotton fiber, especially the cuticle (mainly onsisting of waxes) and primary cell wall (mainly consisting of ectin, protein and xyloglucan). A proper wax removal is necessary for obtaining a high wettability, being a measure for obtaining a good dyeing. Removal of the primary cell wall—especially the pectins—improves wax removal and ensures a more even dyeing. Further this improves the whiteness in the bleaching process. The main chemical used in scouring is sodium hydroxide in high concentrations, up to 70 g/kg cotton and at high temperatures, 80–95° C.; and c. Bleaching; normally the scouring is followed by a bleach using hydrogen peroxide as the oxidizing agent in order to obtain either a fully bleached (white) fabric or to ensure a clean shade of the dye.

A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period which in the case of cold pad-batch might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative rocesses are often used. The most common sizing agent for cotton fabric is based upon starch. Therefore most often, woven cotton fabrics are desized by a combination of hot water, the enzyme α-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath generally ranging from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80° C.–100° C., employing strongly alkaline solutions, pH 13–14, of the scouring agent. Due to the non-specific nature of chemical processes not only are the impurities but the cellulose itself is attacked, leading to damages in strength or other desirable febric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

It is contemplated that the scouring step can be carried out using the polymethylgalacturonase described herein at a temperature of about 40° C.–80° C., preferably 50–70° C., especially 50–60° C., and a pH in the range of 4–10, preferably 5–8, thus substituting or supplementing the known highly causticizing agents. An optimized enzymatic process ensures a high pectin removal and full wettability.

Degradation or Modification of Plant Material

The enzyme described herein is also useful as an agent for degradation or modification of plant cell walls or any pectin-containing material originating from plant cells walls due to the high plant cell wall degrading activity of the polymethylgalacturonases in question.

The polymethylgalacturonase described herein may be used alone or together with other enzymes like glucanases, pectinases and/or hemicellulases to improve the extraction of oil from oil-rich plant material, like soy-bean oil from soy-beans, olive-oil from olives or rapeseed-oil from rapeseed or sunflower oil from sunflower.

The polymethylgalacturonase may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions, The separation process may be performed by use of methods known in the art.

The polymethylgalacturonase may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other component than the galactans like purification of pectins from citrus, improve the feed value, decrease the water binding capacity, improve the degradability in waste water plants, improve the conversion of plant material to ensilage, etc.

By means of an enzyme as described herein it is possible to regulate the consistency and appearence of processed fruit or vegetables. The consistency and appearance has been shown to be a product of the actual combination of enzymes used for processing, i.e. the specificity of the enzymes with which the polymethylgalacturonase is combined. Examples include the production of clear juice e.g. from apples, pears or berries; cloud stable juice e.g. from apples, pears, berries, citrus or tomatoes; and purees e.g. from carrots and tomatoes.

The polymethylgalacturonase may be used in modifying the viscosity of plant cell wall derived material. For instance, the polymethylgalacturonase may be used to reduce the viscosity of feed which contain pectin and to promote processing of viscous pectin containing material. The viscosity reduction may be obtained by treating the pectin containing plant material with an enyme preparation of the invention under suitable conditions for full or partial degradation of the pectin containing material The polymethylgalacturonase can be used e.g. in combination with other enzymes for the removal of pectic substances from plant fibres. This removal is essential e.g. in the production of textile fibres or other cellulosic materials. For this purpose plant fibre material is treated with a suitable amount of the polymethylgalacturonase under suitable conditions for obtaining full or partial degradation of pectic substances associated with the plant fibre material.

Animal Feed Additive

Polymethylgalacturonases as those described herein may be used for modification of animal feed and may exert their effect either in vitro (by modifying components of the feed) or in vivo the polymethylgalacturonase is particularly suited for addition to animal feed compositions containing high amounts of pectin. When added to the feed the polymethylgalacturonase significantly improves the in vivo breakdown of plant cell wall material, whereby a better utilization of the plant nutrients by the animal is achieved. Thereby, the growth rate and/or feed conversion ratio (i.e. the weight of ingested feed relative to weight gain) of the animal is improved.

For further description reference is made to PCT/DK 96/00443 and a working example therein.

Wine and Juice Processing

The enzyme described herein may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme or enzyme preparation may be used in the treatment of mash from fruits and vegetables in order to improve the extractability or degradability of the mash. For instance, the enzyme preparation may be used in the treatment of mash from apples and pears for juice production, anc in the mash treatment of grapes for wine production.

What is claimed is:

1. A process for degradation or modification of fibres, yarn or woven or non-woven fabric comprising plant material, the process comprising the step of subjecting the fibres or fabric to a treatment, in an aqueous solution, with an effective amount of a polymethylgalacturonase enzyme comprising the amino acid sequence of SEQ ID NO:1 or an amino acid sequence having at least 70% sequence identity with SEQ ID NO:1.

2. The process of claim 1, wherein the plant material is cellulosic material.

3. The process of claim 2, wherein the cellulosic material is selected from the group consisting of cotton, rayon/viscose, ramie, hemp, flax/linen, jute, cellulose acetate fibres and lyocell.

4. The process of claim 2, wherein the plant material is recycled waste paper, mechanical paper-making pulps or fibres subjected to a retting process.

5. The process of claim 1 comprising the step of treating fabric during a washing cycle of a machine washing process with a washing solution containing an effective amount of a polymethylgalacturonase enzyme comprising the amino acid sequence of SEQ ID NO:1 or an amino acid sequence having at least 70% sequence identity with SEQ ID NO:1.

6. The process of claim 1, which is a scouring process step.

7. A cleaning or laundering composition comprising an effective amount of a polymethylgalacturonase enzyme comprising the amino acid sequence of SEQ ID NO:1 or an amino acid sequence having at least 70% sequence identity with SEQ ID NO:1, and a surfactant.

8. A process for cleaning a hard surface comprising treating a hard surface with an effective amount of the composition of claim 7.

* * * * *